US012810995B2

(12) United States Patent
Zhang et al.

(10) Patent No.: US 12,810,995 B2
(45) Date of Patent: Nov. 24, 2026

(54) SYSTEM AND METHOD FOR DIAGNOSING DISEASES

(71) Applicant: NovinoAI LLC, Fort Lauderdale, FL (US)

(72) Inventors: David Zhang, Fort Lauderdale, FL (US); Rasoul Sali, Fremont, CA (US); Valerio Zhang, Fort Myers, FL (US)

(73) Assignee: NovinoAI LLC, Fort Lauderdale, FL (US)

( * ) Notice: Subject to any disclaimer, the term of this patent is extended or adjusted under 35 U.S.C. 154(b) by 0 days.

(21) Appl. No.: 19/323,511

(22) Filed: Sep. 9, 2025

(65) Prior Publication Data

US 2026/0011431 A1 Jan. 8, 2026

Related U.S. Application Data

(63) Continuation of application No. 18/614,361, filed on Mar. 22, 2024, now Pat. No. 12,437,857.

(51) Int. Cl.

| | |
|---|---|
| ***G16H 30/20*** | (2018.01) |
| ***G06N 20/00*** | (2019.01) |
| ***G06T 7/00*** | (2017.01) |
| ***G16H 50/20*** | (2018.01) |

(52) U.S. Cl.

CPC ............. *G16H 30/20* (2018.01); *G06N 20/00* (2019.01); *G06T 7/0012* (2013.01); *G16H 50/20* (2018.01); *G06T 2207/20081* (2013.01); *G06T 2207/30024* (2013.01)

(58) Field of Classification Search

None

See application file for complete search history.

(56) References Cited

U.S. PATENT DOCUMENTS

| | | | |
|---|---|---|---|
| 7,702,598 | B2 | 4/2010 | Saidi et al. |
| 8,463,741 | B2 | 6/2013 | Ehlke et al. |
| 9,159,128 | B2 | 10/2015 | Madabhushi et al. |
| 9,779,213 | B2 | 10/2017 | Donovan et al. |
| 10,304,564 | B1 | 5/2019 | Reicher |
| 10,402,699 | B1 | 9/2019 | Chen et al. |
| 10,503,959 | B2 | 12/2019 | Madabhushi et al. |
| 10,769,783 | B2 | 9/2020 | Madabhushi et al. |
| 10,943,345 | B2 | 3/2021 | Barker et al. |
| 11,488,401 | B2 | 11/2022 | Avenel et al. |
| 11,508,168 | B2 | 11/2022 | Allen et al. |
| 11,621,080 | B2 | 4/2023 | Cohen et al. |

(Continued)

OTHER PUBLICATIONS

Barron, Daniel E. Lopez, et al. "Scalable storage of whole slide images and fast retrieval of tiles using Apache Spark." Medical Imaging 2018: Digital Pathology. vol. 10581. SPIE, 2018. (Year: 2018).*

(Continued)

*Primary Examiner* — Samah A Beg

(74) *Attorney, Agent, or Firm* — Amster, Rothstein & Ebenstein LLP

(57) ABSTRACT

The present invention provides a system and method for identifying cancerous tissue based on analysis of histopathologic slides of prostate tissue. In certain embodiments, the system and method classify image information associated with a histopathologic slide based on cancer risk using a first machine learning algorithm trained using a first training set and providing mask information associated with cancer risk that is superimposed on the image data to highlight cancerous or high risk tissue.

15 Claims, 22 Drawing Sheets

(56) References Cited

U.S. PATENT DOCUMENTS

| | | | | |
|---|---|---|---|---|
| 11,705,226 | B2 | 7/2023 | Colley et al. | |
| 11,721,021 | B2 | 8/2023 | Jarrard et al. | |
| 2002/0186882 | A1 | 12/2002 | Cotman et al. | |
| 2016/0171682 | A1 | 6/2016 | Abedini et al. | |
| 2016/0253466 | A1* | 9/2016 | Agaian | G06N 5/043 382/128 |
| 2017/0175169 | A1 | 6/2017 | Lee et al. | |
| 2018/0374210 | A1 | 12/2018 | Barker et al. | |
| 2020/0258223 | A1* | 8/2020 | Yip | G06F 18/21 |
| 2020/0367818 | A1 | 11/2020 | DaCosta et al. | |
| 2021/0090251 | A1 | 3/2021 | Jha et al. | |
| 2021/0246511 | A1 | 8/2021 | Venkat et al. | |
| 2022/0148169 | A1 | 5/2022 | Mermel et al. | |
| 2022/0180626 | A1* | 6/2022 | Song | G06N 3/045 |
| 2023/0105487 | A1 | 4/2023 | Singhal et al. | |
| 2023/0162353 | A1 | 5/2023 | Chiu et al. | |
| 2023/0282011 | A1 | 9/2023 | Teichmann et al. | |
| 2023/0317253 | A1 | 10/2023 | Nie et al. | |
| 2023/0335135 | A1 | 10/2023 | Lefkofsky et al. | |
| 2023/0410301 | A1 | 12/2023 | Rajagopal et al. | |

OTHER PUBLICATIONS

Barker, Jocelyn, et al. "Automated classification of brain tumor type in whole-slide digital pathology images using local representative tiles." Medical image analysis 30 (2016): 60-71. (Year: 2016).*

Lanni, Julianna D., et al. "Tailored for real-world: a whole slide image classification system validated on uncurated multi-site data emulating the prospective pathology workload." Scientific reports 10.1 (2020): 3217. (Year: 2020).*

Tolkach et al., "An International Multi-Institutional Validation Study of the Algorithm for Prostate Cancer Detection and Gleason Grading," npj Precision Oncology, vol. 7, No. 77, 2023, 9 pages.

Esteva et al., "Prostate Cancer Therapy Personalization Via Multi-Modal Deep Learning on Randomized Phase III Clinical Trials," npj Digital Medicine, vol. 5, No. 71, 2022, 8 pages.

Strom et al., "Artificial Intelligence for Diagnosis and Grading of Prostate Cancer in Biopsies: A Population-Based, Diagnostic Study," Lancet Oncol., vol. 21, Jan. 8, 2020, pp. 222-232.

Sali et al., "Deep Learning for Whole-Slide Tissue Histopathology Classification: A Comparative Study in the Identification of Dysplastic and Non-Dysplastic Barrett's Esophagus," J. Pers. Med., vol. 10, No. 141, Sep. 23, 2020, 16 pages.

Cui et al., "Artificial Intelligence and Computational Pathology," Laboratory Investigation, vol. 101, Jan. 16, 2021, pp. 412-422.

Zhang et al., "Implementation of Digital Pathology and Artificial Intelligence in Routine Pathology Practice," Laboratory Investigation, vol. 104, No. 102111, 2024, 11 pages.

Ferrero et al., "HistoEM: A Pathologist-Guided and Explainable Workflow Using Histogram Embedding for Gland Classification," Modern Pathology, vol. 37, No. 100447, Feb. 16, 2024, 12 pages.

Lu et al., "SlideGraph+: Whole Slide Image Level Graphs to Predict HER2 Status in Breast Cancer," Medical Image Analysis, vol. 80, No. 102486, May 25, 2022, 13 pages.

Li et al., "Path R-CNN for Prostate Cancer Diagnosis and Gleason Grading of Histological Images," IEEE Transactions on Medical Imaging, vol. 38, No. 4, Apr. 2019, pp. 945-954.

Barron et al., "Scalable Storage of Whole Slide Images and Fast Retrieval of Tiles Using Apache Spark," Medical Imaging 2018: Digital Pathology, Proc. of SPIE, vol. 10581, 2018, 6 pages.

Linkon et al., "Deep Learning in Prostate Cancer Diagnosis and Gleason Grading in Histopathology Images: An Extensive Study," Informatics in Medicine Unlocked, vol. 24, No. 100582, Apr. 28, 2021, 16 pages.

Mun et al., "Yet Another Automated Gleason Grading System (YAAGGS) by Weakly Supervised Deep Learning," npj Digital Medicine, vol. 4, No. 99, 2021, 9 pages.

* cited by examiner

| Input tissue tiles | | Model output [P(benign \| input tile), P(G3 \| input tile), P(G4 \| input tile), P(G5 \| input tile)] |
|---|---|---|
| 70 |  | [0.999, 0.000, 0.000, 0.001] |
| 72 |  | [0.001, 0.998, 0.000, 0.001] |
| 74 |  | [0.005, 0.007, 0.982, 0.003] |
| 76 |  | [0.005, 0.000, 0.000, 0.995] |

P(benign | input tile): probability of being Benign given the input tile
P(G3 | input tile): probability of being G3 given the input tile
P(G4 | input tile): probability of being G4 given the input tile
P(G5 | input tile): probability of being G5 given the input tile

| Class | Precision | Recall | F1 score | AUC |
|---|---|---|---|---|
| Benign | 0.90 | 0.95 | 0.93 | 0.98 |
| Gleason 3 | 0.91 | 0.86 | 0.89 | 0.96 |
| Gleason 4 | 0.86 | 0.85 | 0.85 | 0.95 |
| Gleason 5 | 0.81 | 0.82 | 0.82 | 0.94 |

FIG. 10

| Class | Precision | Recall | F1 score | AUC |
|---|---|---|---|---|
| Benign | 0.97 | 0.95 | 0.96 | 0.97 |
| Cancer | 0.94 | 0.96 | 0.95 | 0.97 |

FIG. 13

| Architecture | Cohen's kappa |
|---|---|
| Inception V3 | 0.868 |
| Resnet-18 | 0.822 |
| Resnet-34 | 0.847 |
| Resnet-50 | 0.874 |
| VGG16 | 0.861 |
| VGG19 | 0.857 |

FIG. 14

| Models | AUC |
| --- | --- |
| Our model | 0.97 |
| MIL-inspired approach | 0.94 |
| approach proposed in Strom | 0.95 |

FIG. 15

SYSTEM AND METHOD FOR DIAGNOSING DISEASES

CROSS-REFERENCE TO RELATED APPLICATIONS

The present application is a continuation of U.S. patent application Ser. No. 18/614,361, filed Mar. 22, 2024, entitled SYSTEM AND METHOD FOR DIAGNOSING PROSTATE CANCER, the entire content of which is hereby incorporated by reference herein.

BACKGROUND

Field of the Disclosure

The present invention generally relates to a system and method of analyzing histopathological images to identify cancerous tissue. In particular, the system and method utilize machine learning to classify image information and provide a whole slide representation of areas of cancer risk on the histological slide including a mask that overlies the image information data to highlight areas of high risk. The machine learning is based on a training set that includes tagged image information where the tags are provided by an experienced pathologist on both a whole slide level as well as a tile by tile basis.

Related Art

Conventionally, the gold standard for prostate cancer diagnosis is through the microscopic analysis of histopathological images. Different histological features and pattern recognition in biopsies are considered by pathologists in the diagnosis of prostate cancer. The following are examples of such histological features and patterns routinely evaluated by pathologists when diagnosing prostate cancer:

a. Histologic Architecture: Pathologists examine the architectural patterns of the cells. Normal prostate glands have a distinctive glandular structure. Cancerous tissue may exhibit one or more of the following abnormal histological features: disrupted glandular patterns, irregular shapes, and crowding of cells.

b. Nuclear Features: The size, shape, and staining characteristics of cell nuclei are crucial. Cancer cells often have larger and more irregularly shaped nuclei compared to normal cells.

c. Desmoplasia: The interaction between cancer cells and the surrounding stromal tissue is assessed. Invasive cancer may elicit a desmoplastic reaction, leading to changes in the connective tissue.

d. Perineural Invasion: The presence of cancer cells around nerves (perineural invasion) is a characteristic feature of malignancy.

FIG. 1 illustrates example images of histological features and patterns routinely evaluated by pathologists when diagnosing prostate cancer where features a and b are examples of cancerous tissue and features c and d are examples of healthy tissue.

Identifying cancerous regions in histopathology slides, however, is time-consuming and subjective such that results may vary based on the practitioner.

Pathologists also grade histological slides by assigning a Gleason Score, which is an indication of the aggressiveness of the cancer that the pathologist determines based on the microscopic appearance of the tissue. The Gleason Score is based on the patterns of cancer cells in the biopsy and generally ranges from 6 to 10, where higher scores indicate more aggressive cancer. Parameters used to determine Gleason Scores are discussed below.

Primary and Secondary Patterns: The Gleason score is a composite of scores associated with two patterns in a sample. Each pattern is assigned a grade from 1 to 5. The primary pattern is the predominant cancer pattern, and the secondary pattern is the next most common pattern. The sum of scores of the primary and secondary patterns results in the final Gleason score. For example:

Prinary Gleason Score + Secondary Gleason Score = Total Gleason Score

Gleason 3 + 3 = 6

Gleason 3 + 4 = 7

Gleason 4 + 3 = 7

Gleason 4 + 4 = 8

Gleason 4 + 5 = 9

Gleason 5 + 4 = 9

Gleason 5 + 5 = 10

Architectural Patterns: Pathologists examine the architectural patterns of cancer cells in the biopsy. Lower Gleason Scores (6-7) typically exhibit well-formed glands similar to normal prostate tissue. Higher Gleason Scores (8-10) may show an increasing disorganization of glandular structures, with more irregular and fused glands. FIG. 2 provides an exemplary illustration of patterns and their associated Gleason Scores.

Cellular Features: The cellular features of cancer cells are crucial in Gleason Scores. Higher Gleason Scores are associated with more atypical and irregular cells:

Gleason 6: Cells may still resemble normal prostate cells.

Gleason 7: Increasing cellular atypia, with more irregularly shaped nuclei.

Gleason 8-10: Marked cellular atypia, with larger and more irregular nuclei.

Percent Involvement: The percentage of tissue involvement by each pattern is considered. For example, a Gleason 3+4 may have a greater percentage of pattern 4 than pattern 3.

Dominant Pattern: The dominant pattern, which is the one with the highest percentage of involvement, often has a greater impact on the overall prognosis.

As is generally discussed above, assessing biopsy tissue samples can be complicated and subjective and requires accounting for a variety of parameters. As noted above, microscopic review of pathology slides is a time-consuming and labor-intensive process, requiring considerable effort from pathologists. In addition, the subjective nature of the pathologist's analysis is susceptible to error and variability, which can have serious consequences for patients. Indeed, different interpretations of these images that vary from one pathologist to another may lead to inconsistencies in diagnosis and prognosis and differing opinions on the same set of histopathology images.

Accordingly, it would be beneficial to provide a method and system of identifying cancerous tissue using histological slides that avoids these and other issues.

SUMMARY

A method for identifying cancerous tissue based on histopathological slides in accordance with an embodiment of the present disclosure includes: a. obtaining first image information associated with a first histopathological slide of prostate tissue; b. classifying the first image information using a first machine learning algorithm trained using a first training set, where the first image information is an input and the machine learning algorithm provides first classification information associated with the first image information associated with a risk of cancer; c. generating mask information indicating risk of cancer based on the first classification information provided in the classifying step; d. providing the mask information to a user interface, wherein the user interface is configured to display the first image information and the mask information to highlight portions of the first image information associated with risk of cancer.

In embodiments, the histopathological slide is divided into a plurality of tiles and the first image information is associated with a first tile of the plurality of tiles.

In embodiments, the first tile is 512 pixels by 512 pixels.

In embodiments, the first image information is obtained from a database.

In embodiments, the first image information is obtained from a cloud storage system.

In embodiments, the first image information is provided in a format compatible with the machine learning algorithm.

In embodiments, the first image information includes slide ID information associated with a respective slide associated with the first image information and tile location information associated with a position of the tile in the respective slide.

In embodiments, the mask information includes cancer mask information highlighting cancerous tissue and Gleason mask information highlighting tissue with specific Gleason Scores.

In embodiments, the classification information indicates one of the following risks of cancer: a. benign; b. Gleason 3; c. Gleason 4; f. Gleason 5.

In embodiments, the method includes: e. obtaining second image information; f. classifying the second image information using the first machine learning algorithm trained using the first training set, where the second image information is an input and the first machine learning algorithm provides second classification information associated with the second image information associated with the risk of cancer; g. generating updated mask information indicating risk of cancer based on the first classification information and the second classification information; h. providing the updated mask information to the user interface, wherein the user interface is configured to display the first image information, the second image information and the updated mask information to highlight portions of the first image information and the second image information associated with risk of cancer; and i. classifying a whole slide image of the histopathological slide associated with the first image information and the second image information based on the first image information and the second image information.

In embodiments, the step of classifying the whole slide image includes clustering at least the first image information and the second image information and encoding a whole slide image histogram based on the clustered information.

In embodiments, the whole slide image histogram provides a vector associated with the whole slide image and is provided as an input to a second machine learning algorithm trained by the first training set to provide a whole slide image classification.

In embodiments, the method includes storing the first image information, the second image information, the updated mask information and the whole slide image classification in memory configured to store objects and text.

In embodiments, the first training set is stored in memory configured to store objects and text.

A system for identifying cancerous tissue based on histopathologic slides of prostate tissue in accordance with an embodiment of the present disclosure includes: a. first memory configured to store image information associated with a histopathologic slide; b. a machine learning element configured to classify the image information based on risk of cancer and operable connected to the first memory, the machine learning element including: one or more processors; second memory operably connected to the one or more processors and including processor executable code that when executed by the one or more processors, causes the one or more processors to perform steps of: i. obtaining first image information from the first memory; ii. classifying the first image information using a first machine learning algorithm trained using a first training set, where the first image information is an input and the machine learning algorithm provides first classification information associated with the first image information associated with a risk of cancer; iii. generating mask information indicating risk of cancer based on the first classification information provided in the classifying step; and iv. providing the mask information to a user interface, wherein the user interface is configured to display the first image information and the mask information to highlight portions of the first image information associated with risk of cancer on an electronic display operably connected to the machine learning element.

In embodiments, the system may include a formatting element configured to divide the image information associated with the histopathological slide into a plurality of tiles and storing the image information associated with each tile in the first memory, wherein the first image information is associated with a first tile.

In embodiments, the first tile is 512 pixels by 512 pixels.

In embodiments, the first memory is one of a database and a cloud storage system.

In embodiments, the first image information includes slide ID information associated with a respective slide associated with the first image information and tile location information associated with a position of the first tile in the respective slide.

In embodiments, the mask information includes cancer mask information highlighting cancerous tissue and Gleason mask information highlighting tissue with specific Gleason Scores.

In embodiments, the first classification information indicates one of the following risks of cancer: a. benign; b. Gleason 3; c. Gleason 4; c. Gleason 5.

In embodiments, the processor executable code, when executed by the processor of the machine learning element, causes the processor to perform steps of: v. obtaining second image information; vi. classifying the second image information using the first machine learning algorithm trained using the first training set, where the second image information is an input and the first machine learning algorithm provides second classification information associated with the second image information associated with the risk of cancer; vii. generating updated mask information indicating risk of cancer based on the first classification information and the second classification information; viii. providing the updated mask information to the user interface, wherein the user interface is configured to display the first image information and the second image information with the updated mask information to highlight portions of the first image information and second image information associated with risk of cancer; and ix. classifying a whole slide image of the histopathological slide associated with the first image information and the second image information based on the first image information and the second image information.

In embodiments, the step of classifying the whole slide image includes clustering of the first image information and the second image information and encoding the whole slide image as a whole slide image histogram based on the clustered information, wherein the classification of the whole slide image is provided using a second machine learning algorithm trained using the first training set and using the whole slide image histogram as an input to classify the whole slide image.

In embodiments, the system includes a second memory configured to store objects and text, wherein the first image information, the second image information, updated mask information and whole slide image classification are stored in the second memory configured to store objects and text.

In embodiments, the system includes a second memory configured to store objects and text, wherein the first training set is stored in the second memory configured to store objects and text.

BRIEF DESCRIPTION OF THE DRAWINGS

The above and related objects, features and advantages of the present disclosure will be more fully understood by reference to the following detailed description of the preferred, albeit illustrative, embodiments of the present invention when taken in conjunction with the accompanying figures, wherein:

FIG. 10 illustrates a table including the metric values used to validate the classification of tiles using the method of FIG. 4 in accordance with an embodiment of the present disclosure.

FIG. 13 illustrates a table including the metric values used to validate the whole slide image classification using the method of FIG. 4A.

FIG. 14 illustrates a table indicating performance of different machine learning platforms implementing the method of FIG. 4.

FIG. 15 illustrates a table illustrating the performance of different whole slide image classification techniques implementing the method of FIG. 4A.

DETAILED DESCRIPTION

The present invention generally relates to a method and system of using machine learning to analyze histopathological slides of prostate tissue to identify cancerous tissue in prostate tissue. In particular, the method and system provide a mask that may be imposed over a digital image information associate with a whole slide image (WSI) to indicate cancerous or high-risk tissue as well as a whole slide image classification to classify the risk of cancerous tissue in the whole slide as either benign or cancerous.

Figure 1:
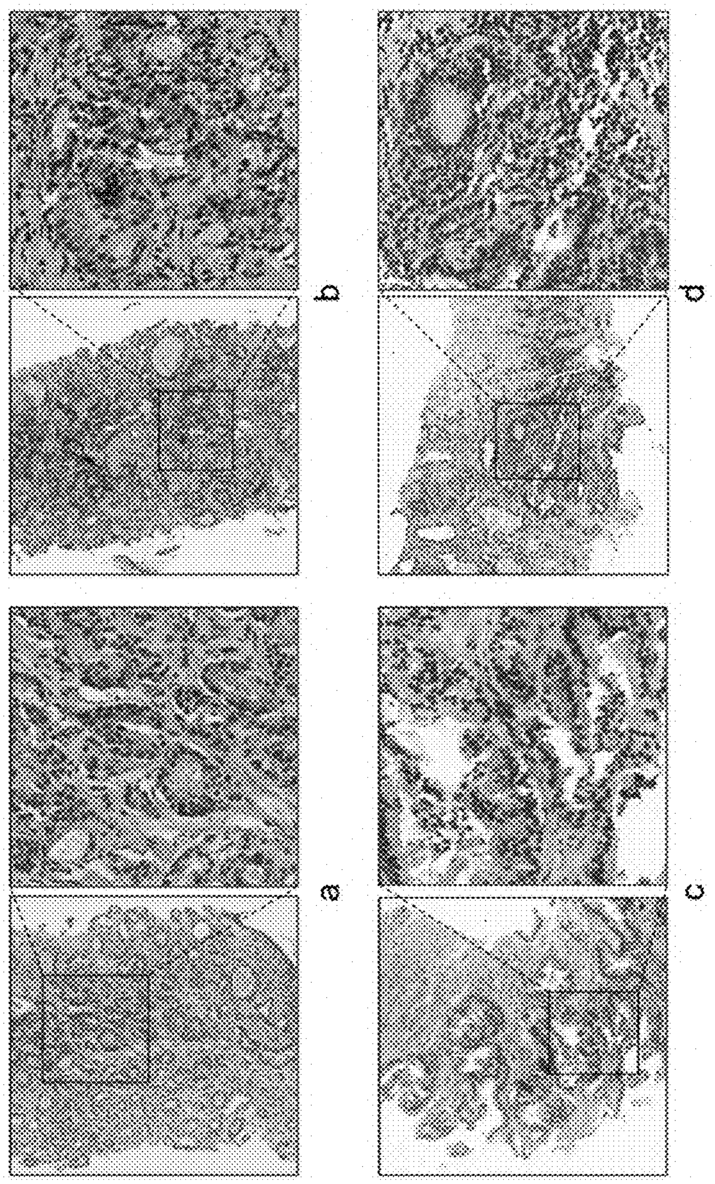
FIG. 1 illustrates exemplary images of cancerous tissue and benign tissue.
Figure 2:
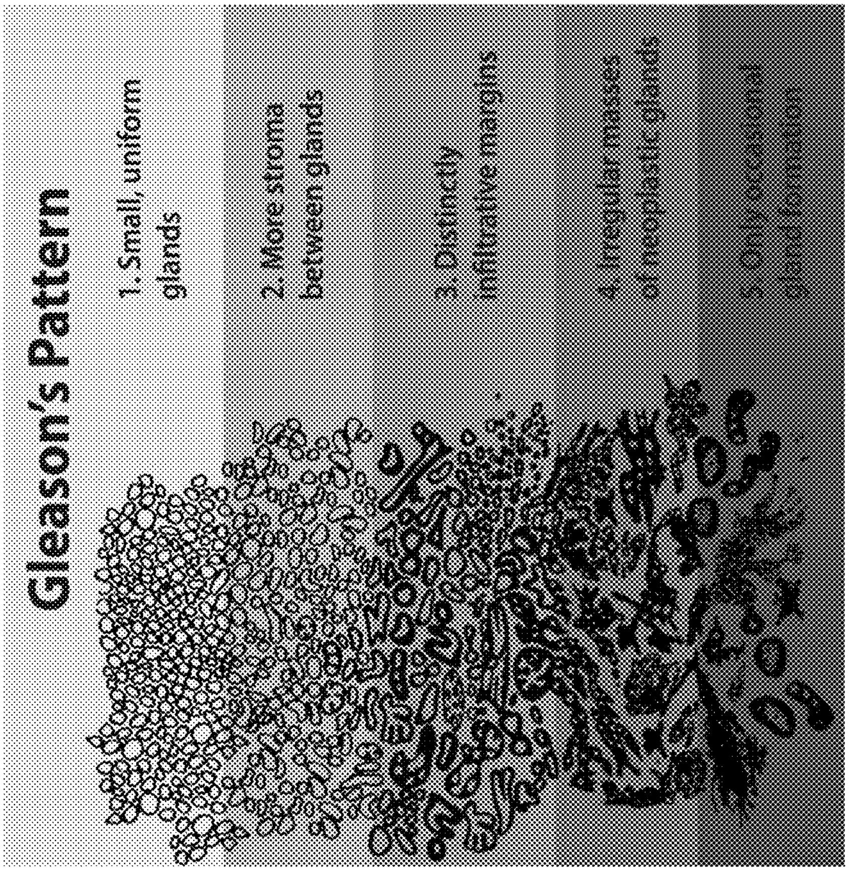
FIG. 2 illustrates exemplary tissue patterns and associated Gleason Scores.
Figure 3:
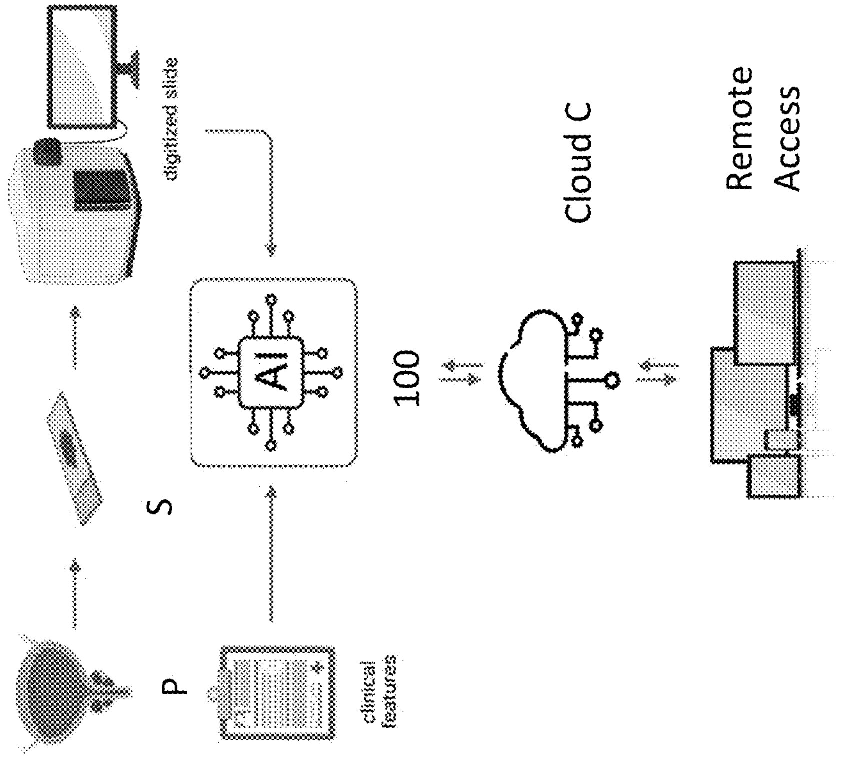
FIG. 3 illustrates an exemplary network topology for use with a system for identifying cancerous tissue in accordance with an embodiment of the present disclosure.

FIG. 3 illustrates an exemplary schematic indicating the relative role of the system for identifying cancerous tissue in the process of diagnosing cancer. As illustrated, a tissue sample is obtained from the prostate P of a patient and a slide S is prepared based on the tissue sample. The slide S may be imaged under magnification as is common in histopathology. In embodiments, the image may be scanned to provide digital image information associated with the whole slide. This image information is obtained by the system 100 (See FIG. 16, for example) and processed using a first machine learning algorithm to classify the tissue. As indicated in FIG. 3, the system 100 may access cloud computing assets and may be accessed remotely such that use of the system is not limited by location or geography. In particular, as is explained below, the system 100 provides mask information that may be applied to the image information to highlight cancerous tissue as well as Gleason Scores related to cancerous tissue which provide an indication of the aggressiveness of the cancer. In embodiments, this information may be provided on a whole slide image basis and may be stored for other purposes and to provide a classification associated with the whole slide to indicate whether the tissue sample is likely cancerous or benign.

Figure 4:
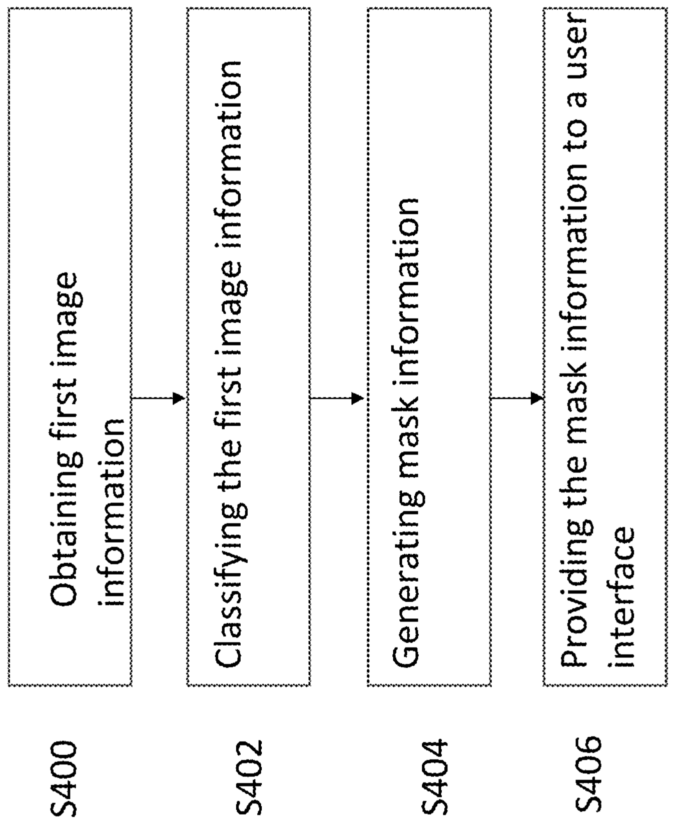
FIG. 4 is an exemplary flow chart for a method of identifying cancerous tissue based on histopathological slides of prostate tissue in accordance with an embodiment of disclosure.

FIG. 4 is an exemplary flow chart illustrating a method of analyzing histologic slide image information to identify cancerous tissue. At step S400, first image information associated with a histologic slide of prostate tissue may be obtained. In embodiments, various slide scanning devices may be used to provide digital image information, including but not limited to Leica's Aperio AT, Roche's DP600 and Heidstar's HDS-MS-200A scanners, to digitize histology glass slides. In embodiments, the image information may be focused on Hematoxylin and Eosin (H&E) stained prostate core needle biopsy images. In embodiments the slides may be scanned at 20× magnification. In embodiments other stains may be used and other magnifications may be used.

In embodiments, a sliding window technique may be used to generate multiple tiles from the scanned whole slide image(s). In embodiments, each tile may be 512 pixels by 512 pixels. In embodiments, each tile may have different dimensions. In embodiments, the digital image information associated with the whole slide is very large, which makes analysis of it difficult and processor intensive. In embodiments, the whole slide image may be broken down into individual tiles to reduce the size of the digital image data that is processed at a time.

Figure 16:
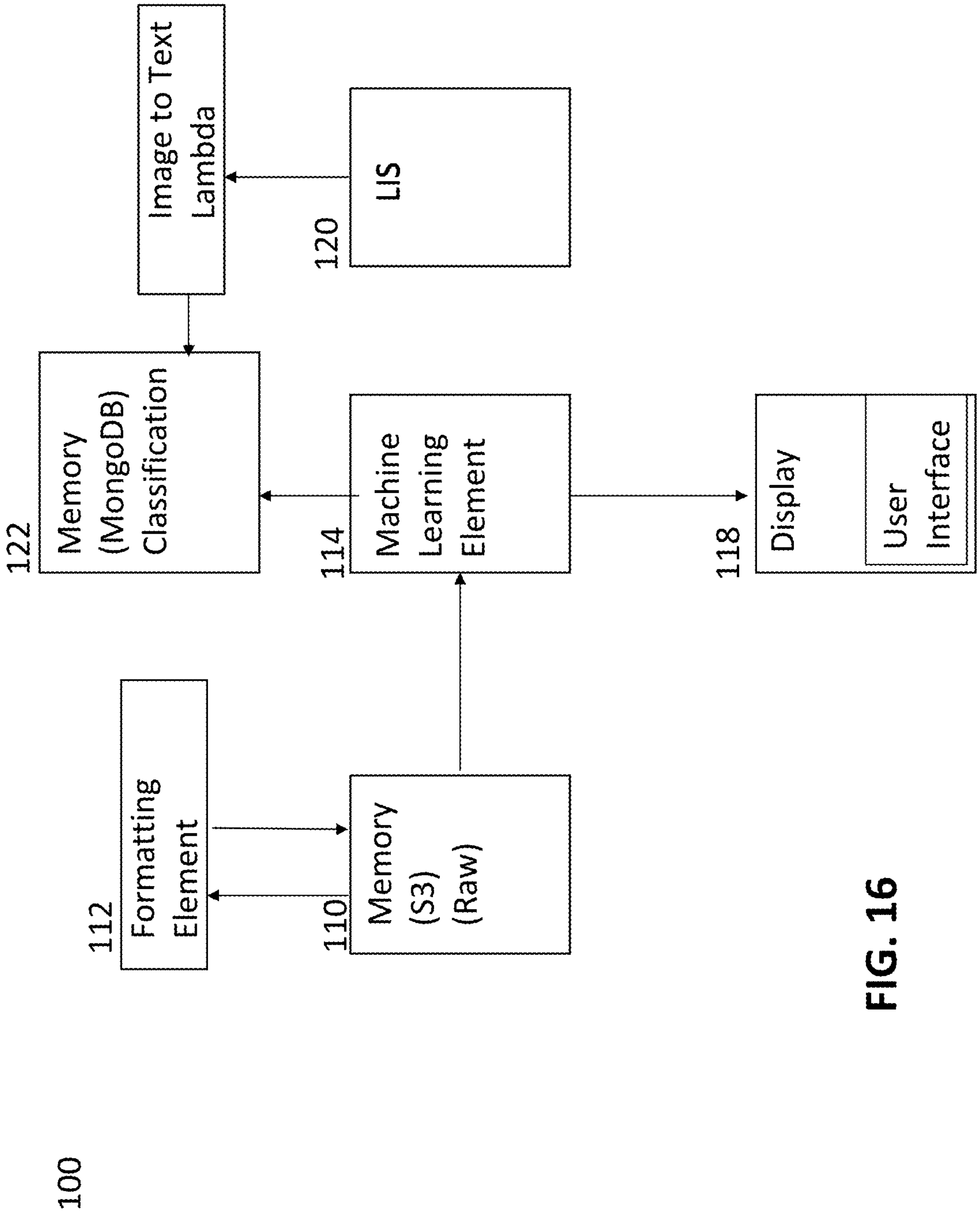
FIG. 16 is a block diagram of a system of identifying cancerous tissue based on histopathological slides of prostate tissue in accordance with an embodiment of the present disclosure.

In embodiments, the digital image information may be stored in and retrieved from a memory (see memory 110, FIG. 16, for example). In embodiments, the memory may be local or may be remote and retrieved via a communication network such as the Internet, for example. In embodiments, the memory 110 may be a cloud-based storage system. In embodiments, the memory 110 may be Amazon Simple Storage Solution (S3) or any other cloud-based storage system. In embodiments, the first image information may be associated with a first tile of a plurality of tiles that constitute the slide. In embodiments, after the first image information, which may be associated with the first tile, is obtained and processed, second image information associated with a second tile may be obtained and processed. This process may be repeated for all tiles associated with a single slide. In embodiments, the first image information may include slide ID information associated with a slide that the image information is extracted from. In embodiments, the first image information may include tile location information associated with a particular tile of the slide associated with that image information. In embodiments, the first image information may include patient information associated with a patient from which the tissue was obtained.

In embodiments, the obtaining step S400 may include retrieving the first image information from memory (memory 110, for example) such as a database, a cloud-based storage, such as S3, or a local memory, to name a few. As noted above, in embodiments, the first image information is associated with a single tile of a plurality of tiles associated with a whole slide image. In embodiments, the first image information may be provided in a desired format, such as deep zoom image DZI which provides the image information in a configuration that allows for viewing at multiple magnifications, etc. While DZI format may be used, it is not necessary and the first image information may simply be associated with a single tile of the digital image information associated with the whole slide image. In embodiments, this tile-by-tile breakdown of the digital image information may be provided in any suitable manner and format. In embodiments, the digital image information may simply be stored in a tile-by-tile format. In embodiments, the first image information may be pre-processed using a formatting element 112 (see FIG. 16) which may be used to convert the image information into tile-by-tile portions suitable for use with the first machine learning algorithm. As noted above, in embodiments, the first image information may be provided in DZI formal, however, this is not required.

In embodiments, upload of the digital image information associated with a whole slide to S3, or another cloud based storage system may trigger application of a program or application, using AWS Lambda, for example, to divide the digital image information associated with the whole slide into tile based portions. As noted above, a DZI format may be used, however is not required. The DZI format is a file format and associated technology developed for efficiently displaying large images on web pages. In general, the format breaks images into tiles at multiple resolution levels to allow users to zoom in and out smoothly. While the present application specifically discusses DZI format, any suitable format may be used provided that they allow for dividing images into tiles. In embodiments, the converted image information may then be stored in the memory S3 or other memory. In embodiments, this converted image information may be the first image information obtained in step S400. In embodiment, the digital image information may be converted into tile-by-tile portions prior to storage in the memory 110 or at another time.

Figure 6:
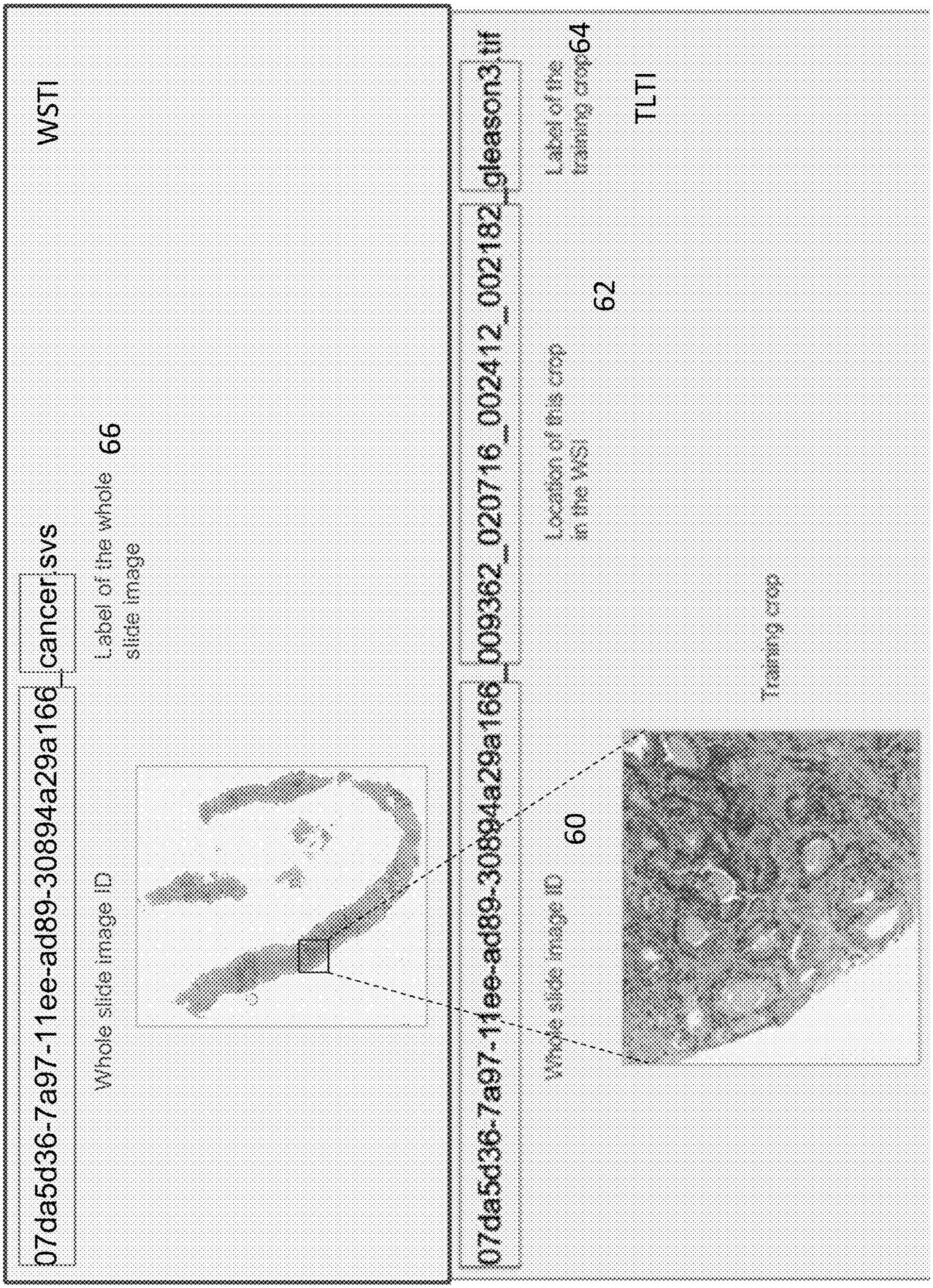
FIG. 6 illustrates exemplary entries in the first training set in accordance with an embodiment of the present disclosure.

In embodiments, at step S402, the first image information, which was obtained in step S400 may be classified using a first machine learning algorithm. In embodiments, the first machine learning algorithm is trained with a first training set. In embodiments, the training set includes image information including tags (classifications) provided by a trained pathologist. In embodiments, the first training set includes both whole slide training information (WSTI) including a benign or cancerous tag or label as well as tile level training information (TLTI) including a tile level classification. FIG. 6 illustrates an exemplary entry in the first training set.

Figure 5:
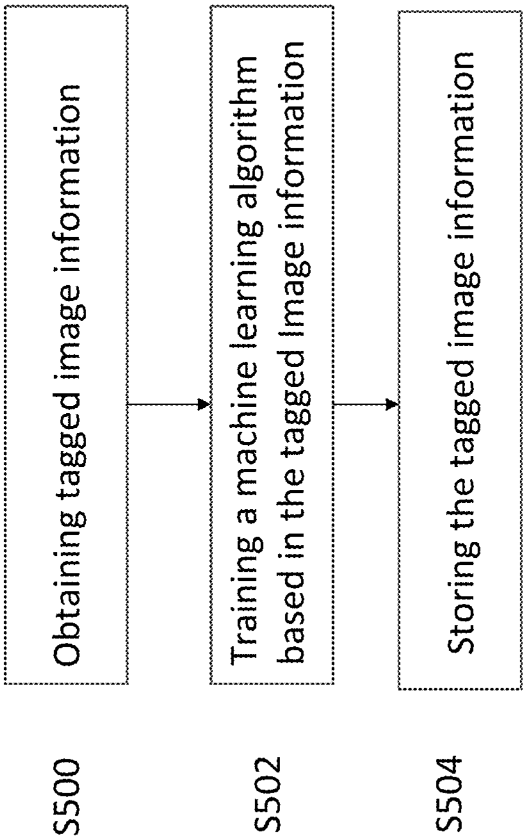
FIG. 5 is an exemplary flow chart illustrating a method for training a machine learning algorithm in accordance with an embodiment of the present disclosure.

FIG. 5 illustrates an exemplary flow chart illustrating a method of training the first machine learning algorithm. At step 500, prior tagged or classified digital image information is obtained. In embodiments, the prior tagged (classified) image information may be a digitized histopathological slide including tags (classifications) that were added by a trained emoryhistopathological slide. As noted above, in embodiments, the training set includes whole slide training information including a cancerous or benign tag as well as tile level training information including cancerous tissue and tags associated with Gleason Scores. In embodiments, the prior image information may be broken up into training crops on a tile by tile bases and tagged training crops may be included in the training set. FIG. 6 illustrates exemplary whole slide training information (WSTI) as well as tile level training information (TLTI). As indicated in FIG. 6, an exemplary training crop of tile level training information may include slide ID information 60, crop location information 62 and the tag (classification) 64 applied by the pathologist. Further, the whole slide training information (WSTI) may include the respective slide ID information associated with the slide as well as a benign/cancerous label 66 associated with the whole slide. That is, in embodiments, the first training set includes both whole slide training information and tile level training information.

At step S502, the training set may be used to train the first machine learning algorithm. In embodiments, the first machine learning algorithm may utilize a convolutional neural network trained based on the first training set. In embodiments, at step S504, the first training set may be stored in memory, for example memory 122 (see FIG. 16, for example). In embodiments, memory 122 may be a database. In embodiments, memory 122 may be a cloud based storage system such as the MongoDB Atlas or Amazon Web Services. In embodiments, memory 122 is configured to save image information as well as text information, such as the classification or tag provided by the pathologist.

In embodiments, exclusion criteria may be implemented to refine the dataset quality used for the first training set. In embodiments, tiles containing less than 30% of actual tissue, as well as those exhibiting undesirable features like tissue folding and blurring artifacts may be excluded from the training set to maintain the integrity and reliability of the dataset, ensuring that only high-quality tissue tiles with relevant content are included.

In embodiments, in step S402, the first machine learning algorithm takes as an input the first image information and provides a classification (tag) for the first image information. In embodiments, as noted above, the first image information is associated with a first tile of a plurality of tiles associated with the whole slide. For each tile, a vector indicating a probability (P) of the tile being classified into each category or classification is provided as an output of the machine learning algorithm. In embodiments, the classifications include benign, Gleason 3 (G3), Gleason 4 (G4) and Gleason 5 (G5). The classification associated with a probability P that is closest to 1 is assigned to that tile. The syntax for the classification follows:

Designated tissue tile category—[probability of benign designation, probability of G3 designation, probability of G4 designation and probability of G5 designation]

Therefore, the following classifications will correspond to the following probabilities:

a. Benign tissue tile category—[1.000, 0.000, 0.000, 0.000]
b. Gleason 3 (G3) tissue tile category—[0.000, 1.000, 0.000, 0.000]
c. Gleason 4 (G4) tissue tile category—[0.000, 0.000, 1.000, 0.000]
d. Gleason 5 (G5) tissue tile category—[0.000, 0.000, 0.000, 1.000]

Figure 7:
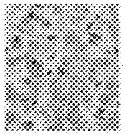
FIG. 7 illustrates an exemplary output generated by the machine learning algorithm in accordance with an embodiment of the present disclosure.
Figure 7:
Figure 7:
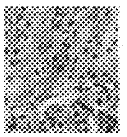
Figure 7:
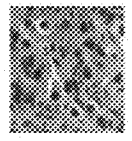

FIG. 7 illustrates examples of input image information (first image information, second image information, etc.) 70, 72, 74, 76 and the corresponding probabilities associated with cancer risk provided for each based on the machine learning algorithm. As noted above, the probability that is closest to 1 will indicate the classification of the image information by the machine learning algorithm. Thus, the top tile 70 in FIG. 7 will be classified as benign, the second tile 72 in FIG. 7 will be classified as Gleason 3 (cancer), the third tile 74 will be classified as Gleason 4 (cancer) and the last tile 76 will be categorized as Gleason 5 (cancer).

In step S404, mask information is generated based on the tile classification. In embodiments, mask information is provided for each tile associated with a respective whole slide image such that the mask information may be applied with the image information associated with the whole slide to highlight areas of concern. In embodiments, in step 404 cancer mask information is generated to provide a cancer mask that highlights cancerous tissue in the whole slide image. The cancer mask information may be generated based on the probabilities provided by the machine learning algorithm as discussed above. In embodiments, Gleason mask information may be generated to highlight tissue associated with specific Gleason Scores again based on the probabilities generated by the machine learning algorithm. Step S404 may be implemented based on post-processing of the probabilities generated by the first machine learning algorithm based on the classification generated. In embodiments, the tile-by-tile classifications may be combined to generate the mask information which corresponds to the whole slide image. In embodiments, the probabilities determined using the first machine learning algorithm are used to generate the mask information to provide a visual indication of likely cancerous tissue as well as visual indications of tissue with different Gleason Scores. In embodiments, the additional processing used to generate the mask information may be performed within a machine learning element (see machine learning element 114 in FIG. 16). In embodiments, the mask information may be generated by a separate processor or computer system operable connected to the machine learning element 114 or otherwise included in or operably connected to the system 100.

Figure 18:
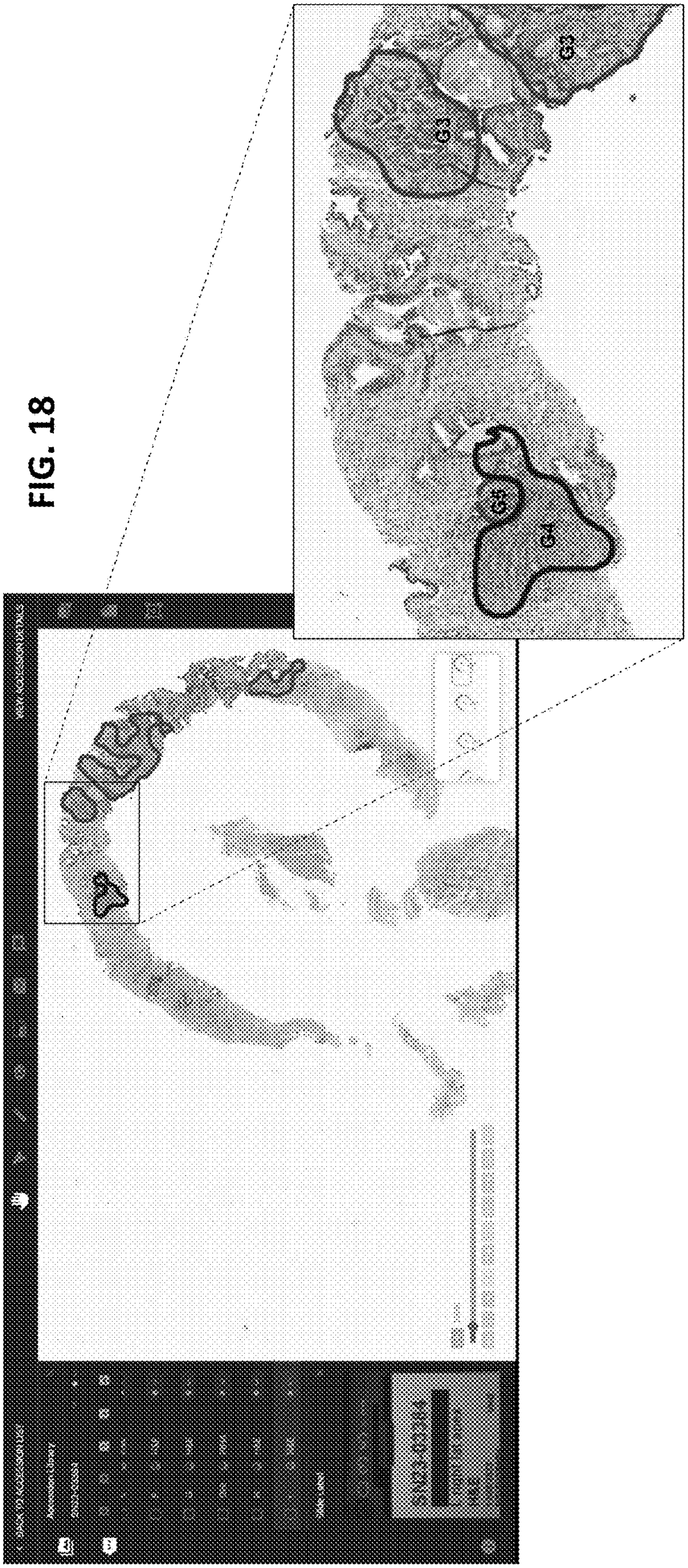
FIG. 18 illustrates an exemplary user interface that may be used to display the cancer mask, the Gleason mask, and the image information including the whole slide image and the whole slide image classification in accordance with an embodiment of the present disclosure.

At step S406, the mask information may be provided to a user interface which may be presented on an electronic display (display 118, for example, FIG. 16) operably connected to the machine learning element 114, or otherwise operably connected to the system 100. In embodiments, the mask information may be superimposed over or combined with the digital image information such that the whole slide image is displayed with the mask information included to highlight cancerous tissue as well as specific Gleason Scores. This representation may be used by a clinician to treat or study prostate cancer. In addition, the mask information and image information may be stored, for example in memory 122 (see FIG. 16) for future access. In embodiments, the user interface allows a user to interact with the whole slide image provided based on the digital image information as well as the mask information. In embodiments, a user may modify the mask information to correct a perceived error. In embodiments, a user may identify particular structures or morphological features in the whole slide image using the user interface. In embodiments, the user interface may include tools to allow the user to measure or otherwise quantify different tissue in the whole slide image. In embodiments, the user may make notes or observations that will be recorded with the image information and the mask information. In embodiments, a user may select portions of the whole slide and mask to be enlarged for more detailed study, as is generally indicated in FIG. 18. As noted above, the mask information and whole slide image may be used to provide an accurate Gleason Score by calculating the percentage of the total assigned to each Gleason Score.

In embodiments, the steps S400 and S402 may be repeated with respect to second image information to provide second classification information which may be associated with a second tile of a respective slide. Thereafter, step S404 is repeated to provide updated mask information based on the first classification information and the second classification information. At step S406, the updated mask information may be provided to the user interface and the user interface may display the first image information, the second image information and the updated mask information to highlight portions of the first image information and the second image information associated with risk of cancer.

This process may be repeated until all tiles associated with a respective slide are processed and the mask information is updated to include all tiles.

As is discussed in further detail below, the results provided by the classification in step S404 using the first machine learning algorithm are accurate, however, they are probabilities and are not perfect and do not take into account the whole slide. In embodiments, the inclusion of even one incorrectly identified tile in a slide may result in an incorrect identification of the tissue. Accordingly, in order to provide an accurate indication of cancer risk based on the whole slide image (WSI), the classifying step 402 may include classifying the whole slide. In embodiments, a second classifying step may be provided to classify the whole slide image (WSI). In embodiments, a second classifying step may be provided before or after the step of generating the mask information S404.

In embodiments, whole slide image classification may be based on a clustering analysis of the tiles discussed above to provide a label (classification) for the whole slide, as either benign or cancerous. In embodiments, whole slide image classification involves encoding each whole slide image. In embodiments, a histogram based encoding technique may be used. In embodiments, each WSI $X_i$ i=1, 2, . . . , N is considered as a set of tissue tiles:

$$X_i = \{x_1, x_2, \dots, x_{n_i}\}$$

In embodiments, a function M may be used to map each image tile $x \in X_i$ to a concept $c_k$, k=1, 2, . . . , K. In embodiments, all concepts may be organized as a vocabulary $V=\{c_1, c_2, \dots, c_K\}$. Consequently, WSI $X_i$ is mapped to histogram $H_i=(h_1, h_2, \dots, h_k)$ as follows:

$$H_i = \frac{1}{|X_i|}\sum_{x \in X_i} M(f_\psi(x, V)),\ i = 1,2, \dots, N$$

The k-th bin in $H_i$ is calculated as follows:

$$h_k = \frac{1}{|X_i|}\sum_{x \in X_i} P(c_k \mid f_\psi(x)),\ k = 1,2, \dots, K$$

In embodiments, $P(c_k|f_\psi(x))$ is the likelihood that the embedding vector of tissue tile x belongs to concept $c_k$. In other words, the image-level histogram (see FIG. 8B, for example) is the normalized frequency of each concept $c_k$ (cluster) in the corresponding whole slide image.

In embodiments, the clustering discussed above is unsupervised such that clustering may result in any number of clusters (concepts) and is not limited to the classifications discussed above. In embodiments, the clusters may each be associated with a particular feature in the image data, in particular, morphological features in the slide. That is, in embodiments, each cluster (concept) is associated with a morphological feature, however, the specific nature of that feature remains unidentified. While a pathologist may be able to identify the feature by looking at the tiles in each cluster, it is unlikely that they would do so accurately since the traits in each cluster are based on identification of data patterns using the clustering analysis rather than pathological principles. Indeed, in embodiments, the morphological features that are associated with each cluster may not be visible to a pathologist viewing the tiles in the cluster. In embodiments, this clustering approach provides for a data based analysis of the whole slide that provides results that would not be visible to a pathologist.

In embodiments, the clusters are used to generate a whole slide level histogram using the equations described above, which provides a vector representative of the whole slide image. In embodiments, this may be accomplished by calculating the number of tiles associated with each cluster and providing the histogram based on this information. In embodiments, this histogram is representative of the WSI, however, the amount of data associated with it is substantially smaller than the digital image information associated with the whole slide image. In embodiments, by reducing the whole slide image information into a vector associated with the whole slide, the WSI classification takes into account data associated with the whole slide at a greatly reduced size which accelerates and simplifies processing. In embodiments, each slide will have an associated histogram and the histogram may be used as an input to a second machine learning algorithm to classify the whole slide image as cancerous or benign based on a second machine learning algorithm trained using the first training set, and specifically, using the slide level training information.

In embodiments, the classification approach is inspired by a bag of features framework, or specifically, a bag-of-words scheme used for text categorization and text retrieval. The approach differs from the bag of features framework in that Gaussian Mixture Models (GMMs) may be used to cluster tile-level embeddings ($f_\psi(x)$) in different clusters ($c_k$, k=1, 2, . . . , K) as generally indicated in FIG. 8A, for example. Given this approach, $P(c_k|f_\psi(x))$ is the posterior probability of cluster k-th given embedding vector $f_\psi(x)$, which in GMM is derived from the following equation:

$$P(c_m \mid f_\psi(x)) = \frac{\pi_m \cdot N\left(f_\psi(x) \mid \mu_m, \sum_m\right)}{\sum_{k=1}^{K} \pi_k \cdot N\left(f_\psi(x) \mid \mu_k, \sum_k\right)},\ m = 1,2, \dots, K$$

where $\pi_m$ is the probability of component m, and N is the multivariate Gaussian distribution with mean $\mu_m$ and covariance matrix $\Sigma_m$. After encoding the WSI using aggregation of patch-level labels based on the clustering whole slide image-level histograms are used to predict the WSI-level labels classifications (benign, cancer) as generally indicated in FIG. 8C. FIG. 8C illustrates a generic classification schematic and the present application is not limited to the illustrated schematic. That is, the histogram may be processed to identify suspicious clusters which may indicate cancerous tissue. In embodiments, as discussed above, the first training set may be used to train the second machine learning algorithm to classify the whole slide image using the histogram as an input. In embodiments, the second machine learning algorithm may be trained using the first training set, specifically the whole slide level training information discussed above with respect to FIG. 6. Since the above approach examines all tissue tiles within the slide and takes into account the variability within the slides, it provides superior results when compared to other approaches, as will be discussed further herein. In addition, since the above approach provides for a data based analysis of the whole slide image information, it identifies features that may not be visible to a human pathologist.

Figure 4A:
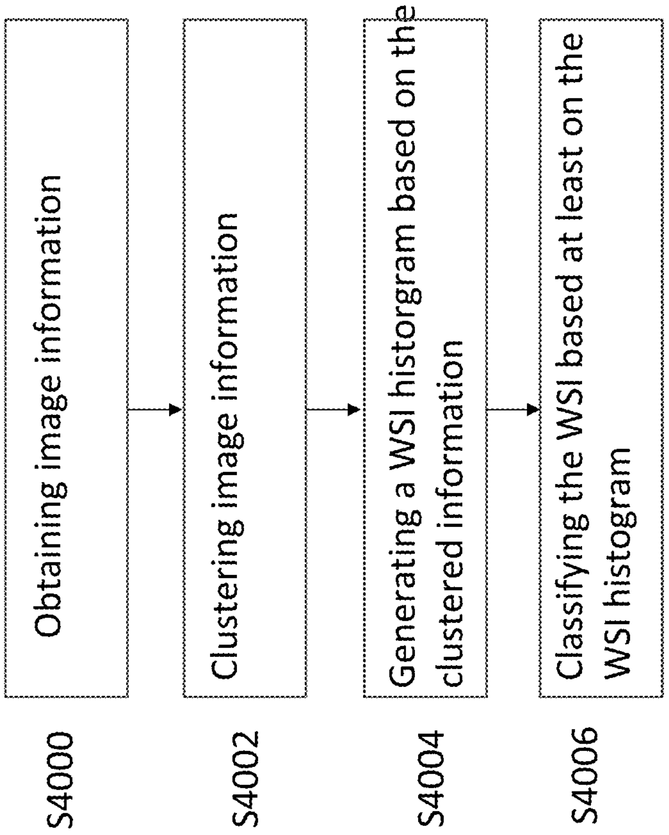
FIG. 4A is an exemplary flow chart for a method of classifying a whole slide image of a histopathological slide in accordance with an embodiment of the present disclosure.

FIG. 4A illustrates an exemplary flow chart illustrating a method of classifying a whole slide image. In embodiments, at step S4000 the image information (first, second third, etc.) associated with a slide may be obtained. In embodiments, at step S4002, the image information is clustered. In embodiments, as noted above, the clustering is unsupervised such that the number of clusters is based purely on the image information and is independent of the classifications provided by the machine learning algorithm on a tile-by-tile basis. As noted above, the clustering may be based on the above equations. As noted above, each cluster may be associated with a morphological feature in the whole slide image. In embodiments, at step S4004, a whole slide image histogram is generated based on the clustered image information and the process described above. In step S4006, the whole slide image is classified as cancerous or benign based on the whole slide image histogram. In embodiments, the classification may be provided using a second machine learning algorithm trained using whole slide training information of the first training set and using the whole slide image histogram as an input to provide a classification of the whole slide image as cancerous or benign as an output.

In embodiments, a multiple instance learning (MIL) approach may be used as an alternate WSI classification approach. In this methodology, a WSI is classified as cancerous if at least one tissue tile within the image is labeled as cancerous. Conversely, the WSI is classified as benign only if all tissue tiles are identified as benign. One drawback of this approach is that it presumes that the tile-level label adequately represents the content of the slide. In some cases, a slide may contain predominantly benign tissue tiles with only a few cancerous ones but would be labeled cancerous. Further, as noted above, a single false positive tile or false negative tile could result in an improper classification. The MIL approach does not provide fine-grained labeling which may limit the discriminative power of an MIL classifier. In contrast the approach used in the present application takes into account all image information associated with a particular slide so that variability within the slide is taken into account. In this approach, as noted above, variability within the slide is accounted for by allocating image information to different clusters and then representing the slide as a histogram in which each bin value signifies the frequency of tissue associated with the corresponding cluster.

In embodiments a method which incorporates various WSI-level features as is described in Ström, Peter, Kimmo Kartasalo, Henrik Olsson, Leslie Solorzano, Brett Delahunt, Daniel M. Berney, David G. Bostwick et al. "Artificial intelligence for diagnosis and grading of prostate cancer in biopsies: a population-based, diagnostic study." *The Lancet Oncology* 21, no. 2 (2020): 222-232 may be used. In such an approach, for a slide with n tissue tiles, slide-level features were extracted from an n×c matrix of class-wise probabilities estimated by tile-level CNN for 4 classes (benign, Gleason 3, Gleason 4, Gleason 5). These features include Sum, Median, Maximum, 99.75th percentile, 99.50th percentile, 99.25th percentile, 99th percentile, 98th percentile, 95th percentile, 90th percentile, 80th percentile, 10th percentile and the count of tissue tiles with tumor probability exceeding 0.9, 0.99, and 0.999. The approach involves training a classifier on these features to make the final WSI label prediction. One problem associated with the approach is that while slide-level features are interpretable, they are not data-driven. The approach uses certain slide-level features to train a classifier, however, these selected features may not be sufficient to represent the totality of the data.

Alternatively, an end-to end approach, like that discussed in Sharma, Yash, Aman Shrivastava, Lubaina Ehsan, Christopher A. Moskaluk, Sana Syed, and Donald Brown. "Cluster-to-conquer: A framework for end-to-end multi-instance learning for whole slide image classification." In *Medical Imaging with Deep Learning*, pp. 682-698. PMLR, 2021 may be used. These approaches leverage tile-level predictions to determine the label of the WSI. The whole model is trained in an end-to-end fashion. However, a notable challenge with such methods is the requirement for a substantial number of WSIs during training, a condition that may not always be met due to limited data availability. Thus, one serious drawback of this approach is that it requires a large amount of labeled whole slide images and is computationally intensive both for training and operation which may be a barrier to use.

In embodiments, the approach described above with respect to FIG. 4A provides superior results after testing. For testing purposes, a random partition of 75% of training set tiles was used for training the machine learning algorithm while 25% were reserved for validation. This division of the training set safeguards the integrity of the validation process and prevents contamination from patient samples already incorporated into the training dataset. All tissue tiles were associated with a particular patient assigned exclusively to either the training or validation set, thereby ensuring the evaluation is entirely independent of the data used for its training. As a result, reliability and generalizability of the machine learning algorithm is preserved as it minimizes any potential biases introduced by overlapping patient data in both training and validation phases.

Four typical evaluation metrics were used: the area under the ROC curve (AUC), Precision, Recall, and F1 score. For testing, the machine learning model was implemented using the PyTorch platform and trained with NVIDIA Tesla V100 GPUs and using cross-entropy loss for 30 epochs. The Stochastic Gradient Descent (SGD) optimizer at a learning rate of 0.001 with a batch size of 32 was employed. Tissue tiles were resized to 256×256 px for training the model. Color and data augmentation approaches were employed through the training process to enhance performance.

Figure 11:
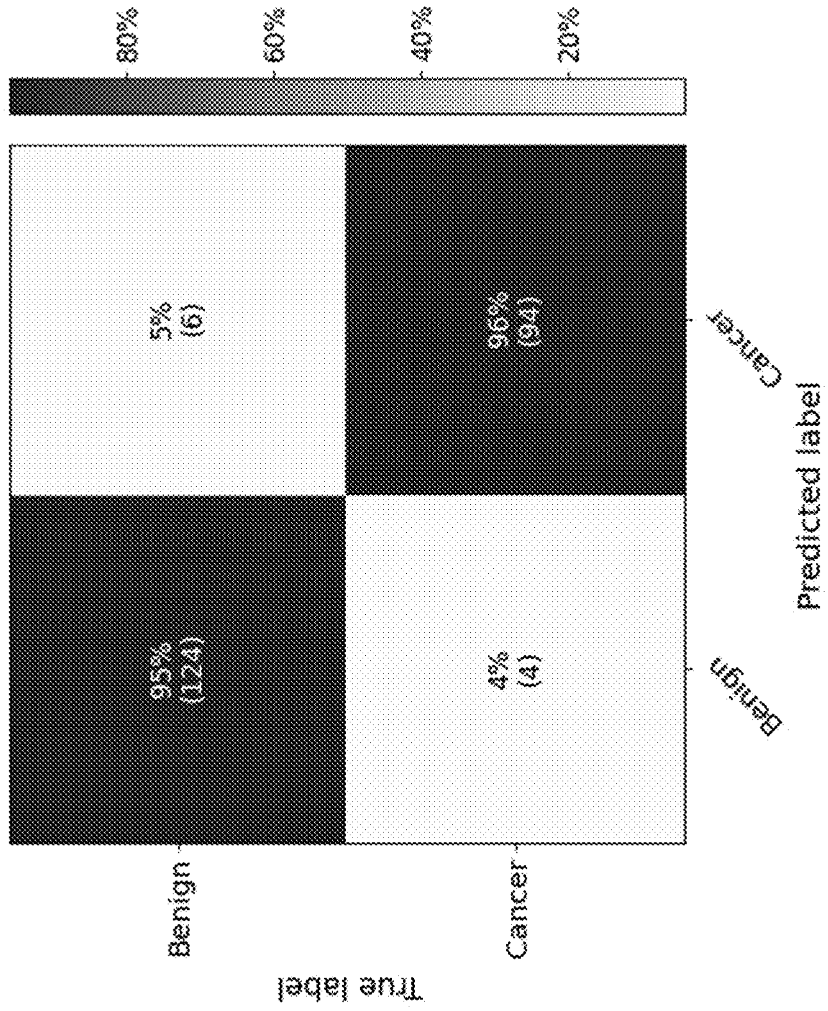
FIG. 11 illustrates a confusion matrix generated based on applying the whole slide image classification approach of FIG. 4A in accordance with an embodiment of the present disclosure.

The validation set included 228 WSIs (benign: 130, cancerous: 98) from 15 patients. In total, there were 1,945, 296 (benign: 546,927, Gleason 3: 483, 103, Gleason 4: 502,566, Gleason 5:412,700) tissue tiles in the validation set. FIG. 10 illustrates a confusion matrix associated with the performance of the first machine learning algorithm analyzing the validation set. FIG. 11 illustrates the metrics associated with the evaluation.

Figure 12:
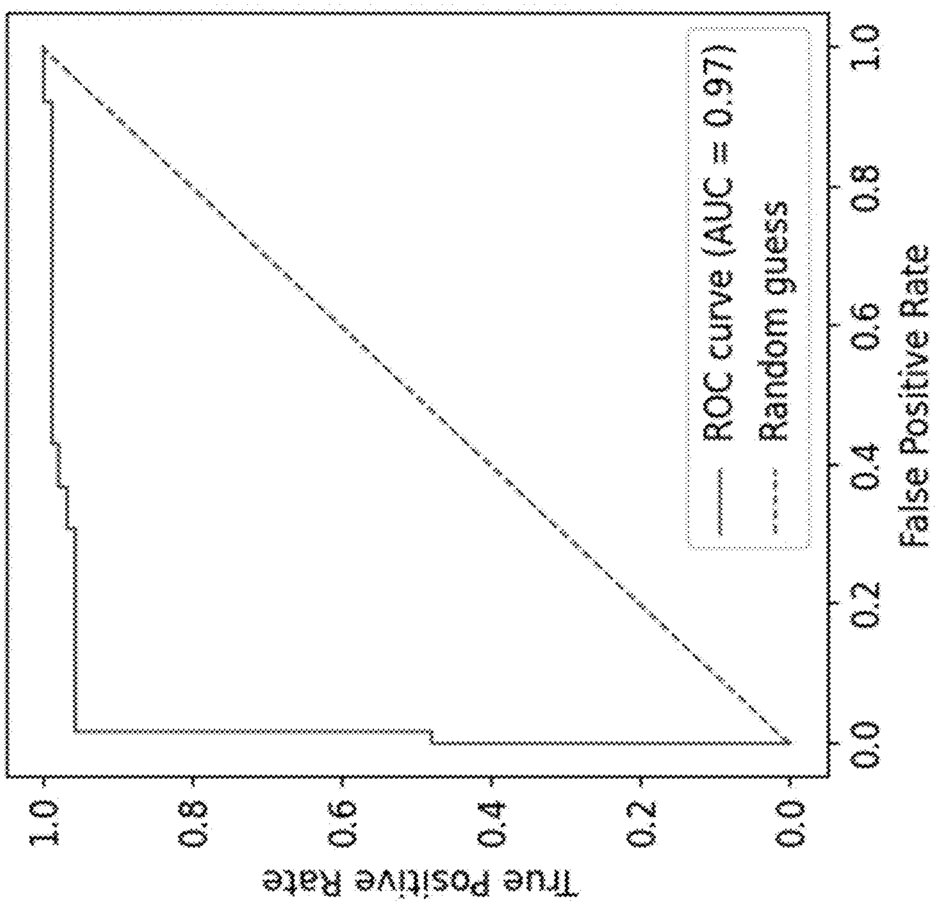
FIG. 12 illustrates a confusion matrix associated with using the machine learning algorithm of FIG. 4A providing whole slide image (WSI) classification.

With respect to WSI classification, FIG. 12 illustrates a confusion matrix summarizes performance of the WSI classification using the second machine learning algorithm and the approach discussed above. FIG. 13 is a chart illustrating the ROC curve associated with the WSI classification discussed above.

FIG. 14 is a chart of the relative performance of different machine learning architectures in conjunction with the method of FIG. 4. As indicated in FIG. 14, in embodiments the Resnet-50 architecture provides the best results. That said, in embodiments, other machine learning architectures or platforms may be used.

FIG. 15 is a chart comparing results of the WSI classification approach discussed above with respect to FIG. 4A with the alternative approaches discussed above. As can be seen in FIG. 15, the approach of FIG. 4A provides the best results. That said, in embodiments, other approaches may be used.

Figure 8:
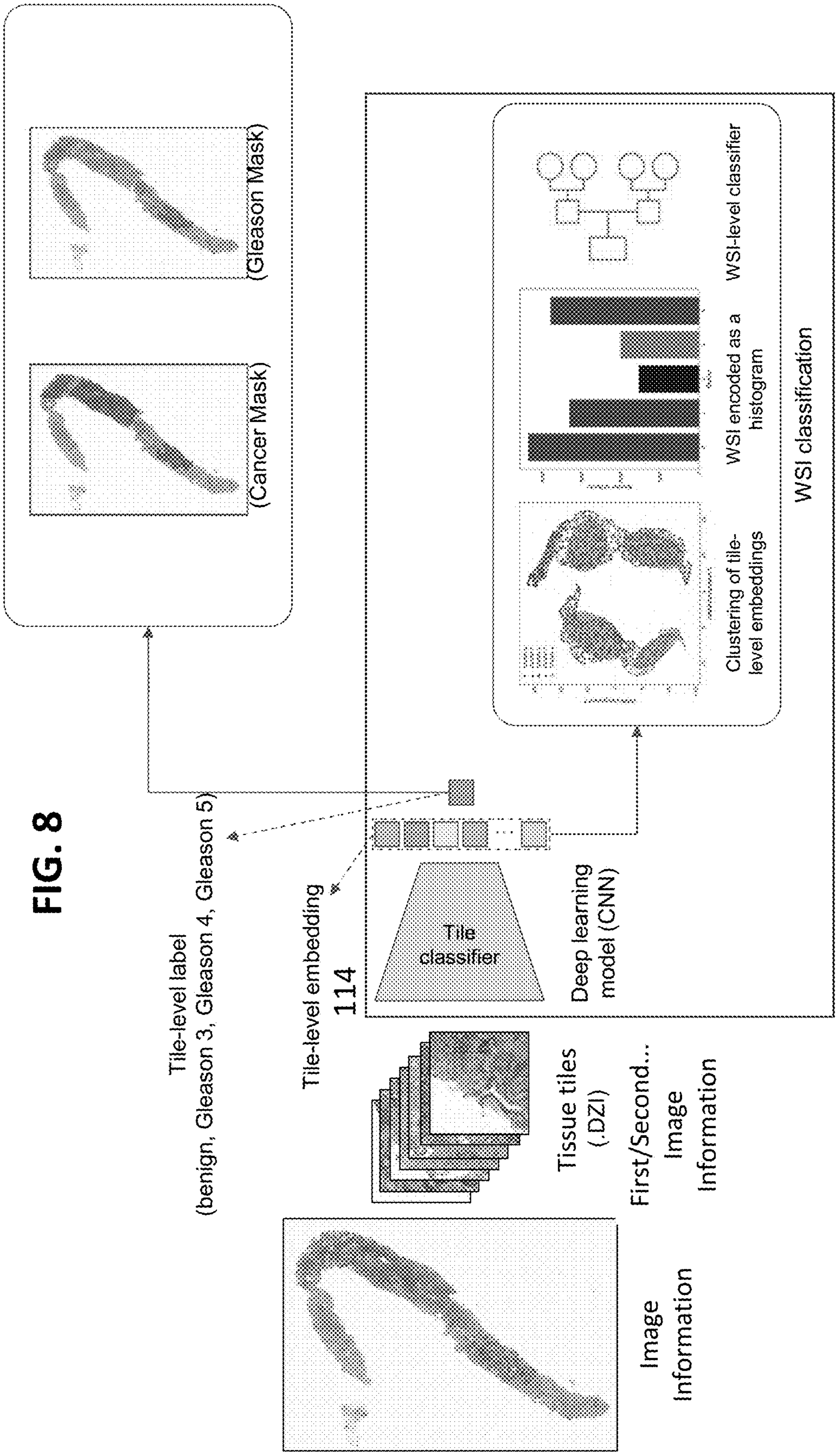
FIG. 8 illustrates a schematic representation of the method of FIGS. 4 and 4A in accordance with an embodiment of the present disclosure.
Figure 8A:
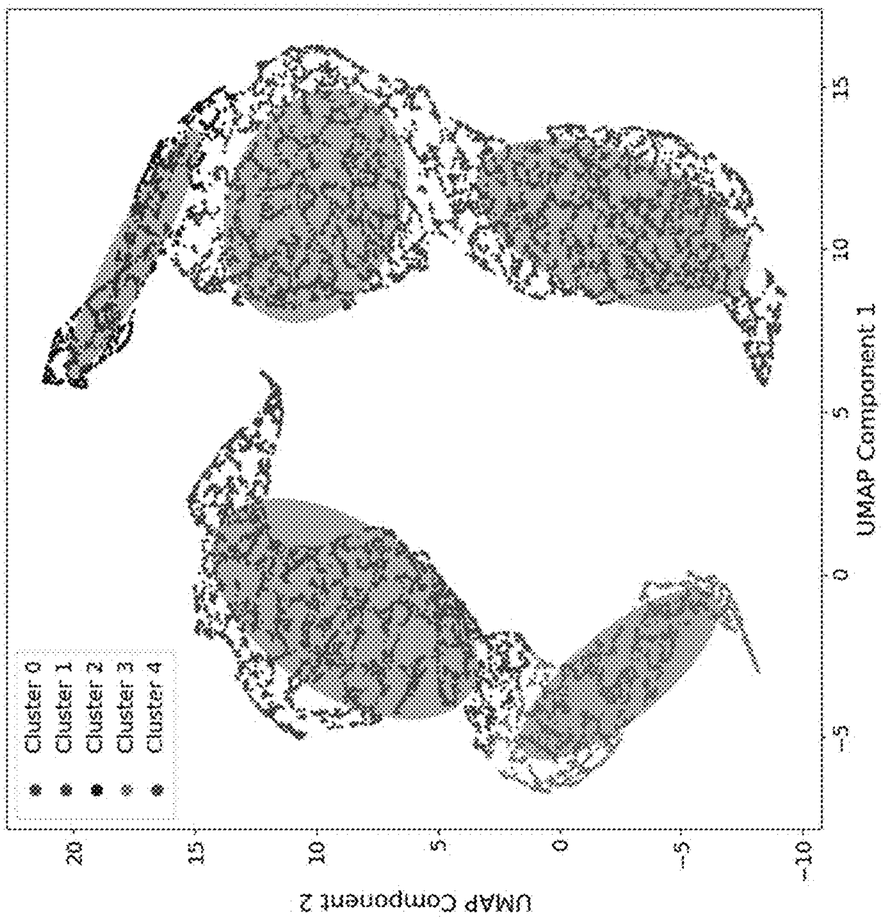
FIG. 8A illustrates a more detailed view of the clustering illustrated in FIG. 8 exemplary clustering of tile classification information associated with a whole slide image in accordance with an embodiment of the present disclosure.
Figure 8B:
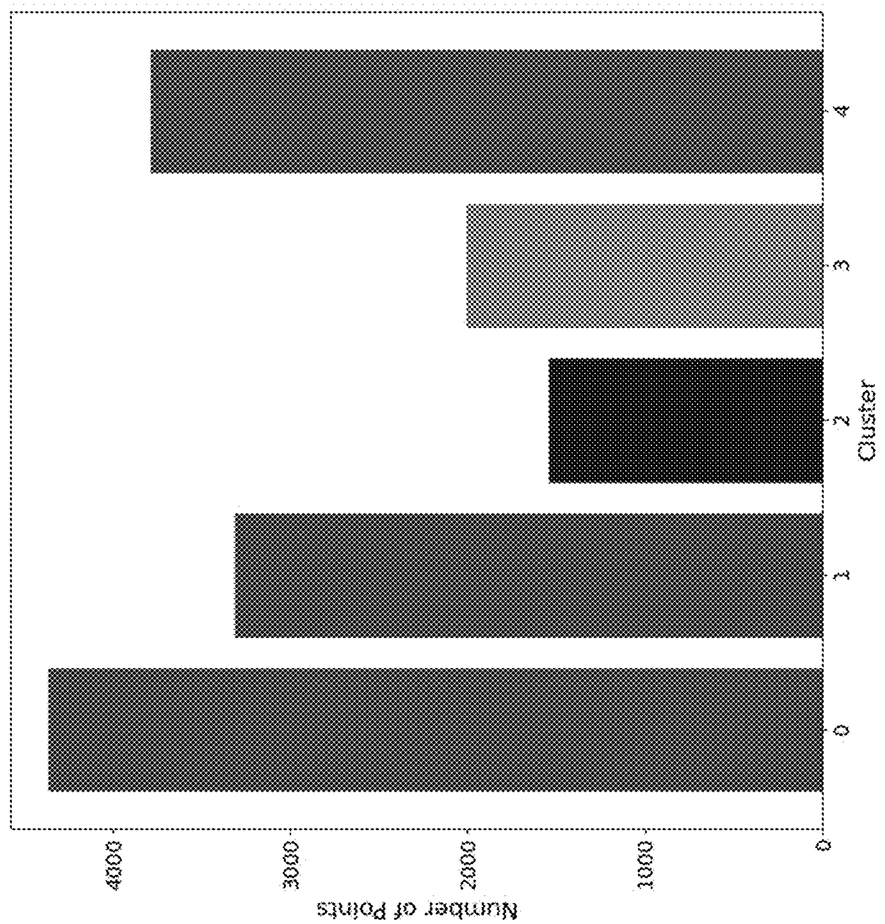
FIG. 8B illustrates an exemplary histogram that may be generated based on clustering shown in FIG. 8A in accordance with an embodiment of the present disclosure.
Figure 8C:
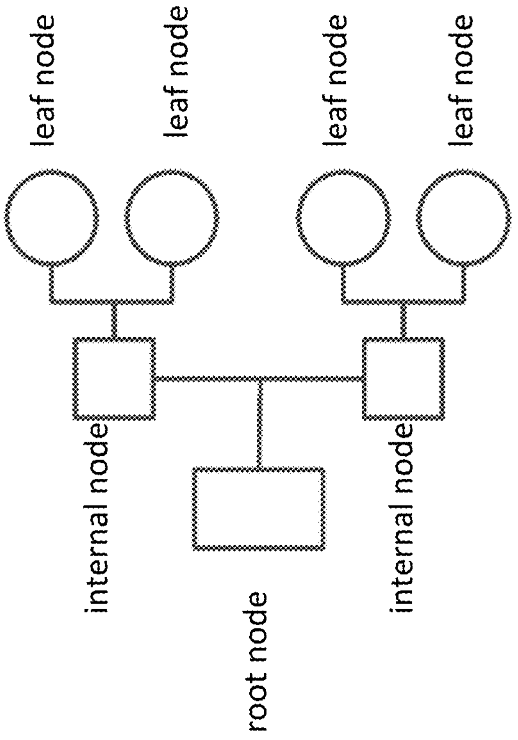
FIG. 8C illustrates an exemplary classification approach that may be used to classify the whole slide image based on the histogram in accordance with an embodiment of the present disclosure.
Figure 9:
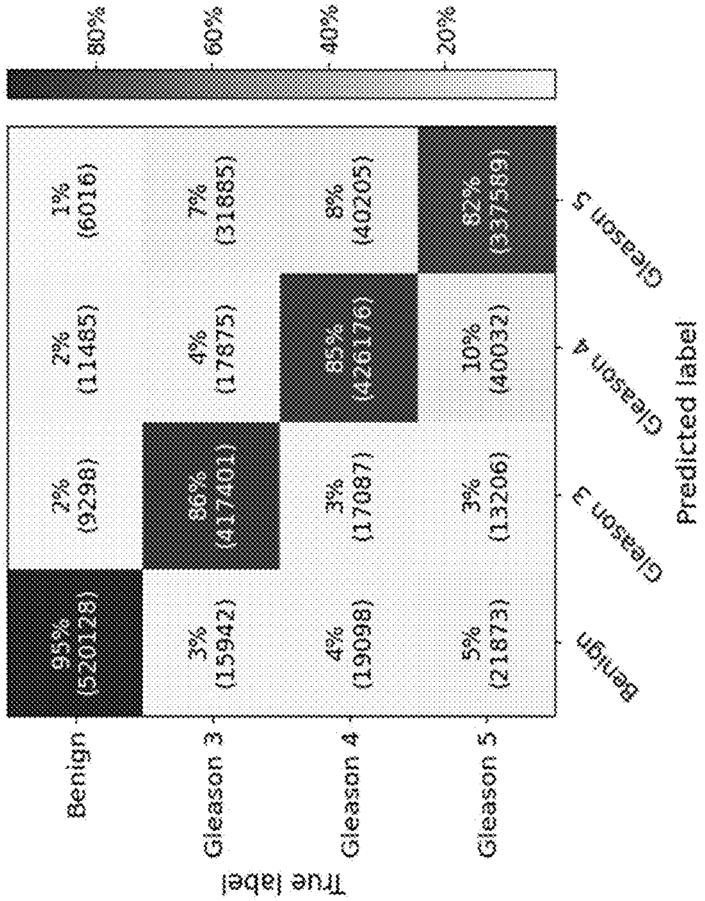
FIG. 9 illustrates a confusion matrix provided based upon application of the method of FIG. 4 to a validation set of image information.

FIG. 8 illustrates a schematic representation of the method described with reference to FIGS. 4 and 4A. As indicated in FIG. 8, digital image information associated with a whole slide (whole slide image WSI) may be provided from a variety of scanners. In an embodiment, the image information may be converted plurality of tiles, which may or may not be in DZI format. The tile-by-tile image information (first image information, second image information, etc.) is classified by the first machine learning algorithm, which is trained using a first training set, to provide a classification for each tile (benign, Gleason 3, Gleason 4, Gleason 5) while a second machine learning algorithm provides a whole slide image classification as noted above. Mask information is generated based on the classifications to provide a cancer mask (see FIG. 17A) and a Gleason mask (See FIG. 17B) as indicated in FIG. 8.

A system 100 for identifying cancerous tissue in accordance with an embodiment of the present application is illustrated in FIG. 16. In embodiments, digital image information associated with the prostate tissue may be provided to and stored in a first memory 110. In embodiments, the first memory 110 may be a database. In embodiments, the first memory 110 may be a cloud based storage system. In embodiments, the first memory 110 may be an object storage system such as Amazon's Simple Secure Storage (S3). In embodiments, this digital image information may be obtained from a variety of sources and scanners. In embodiments, digitizing histopathological slides is common in identifying cancerous tissue d and there are a variety of scanners and scanning techniques that may be used to provide digital image information associated with a slide.

In embodiments, the upload of the image information to the first memory 110 may trigger implementation of a formatting element 112 that may be used to format the image data for use with the machine learning element 114. In embodiments, the upload of the digital image information may trigger operation of the formatting element 112 that may be used to divide the digital image information associated with a respective slide into a plurality of tiles. In embodiments, a DZI format may be used, but is not required. In embodiments, AWS Lambda Zoom may be implemented to convert the image information into tiles by the formatting element 112 in which the image information associated with each slide is divided into a plurality of tiles. In embodiments, digital image information is provided for each tile and includes slide ID information associated with a slide from which the tile is derived and tile location information associated with a location of the tile within the slide. In embodiments, the digital image information may be provided in a tile-by-tile manner such that the formatting element 112 may not be necessary.

In embodiments, the machine learning element 114 may obtain first image information from the memory 110. In embodiments, the first image information may be in DZI format associated with a first tile. In embodiments, the machine learning element 114 is configured to classify the first image data using a first machine learning algorithm that is trained using the first training set discussed above. In embodiments, the first machine learning algorithm may be implemented using a convolutional neural network. In embodiments, the first image information is an input and the first machine learning algorithm element provides a classification associated with the first image information based on the first machine learning algorithm trained using the first training set. In embodiments, the machine learning element 114 performs the obtaining step 400 discussed above and obtains the first image information and then classifies the first image information in accordance with step S402 discussed above. The machine learning element 114 may classify a plurality of tiles by repeating the process with respect to second image information associated with a second tile, third image information associated with a third tile and so on. In embodiments, all of the tiles associated with a whole slide image are processed by the machine learning element 114. In embodiments, as noted above, the first image information, second image information and so on, is provided with a probability associated with a classification (benign, G3, G4, G5) on a tile by tile basis such that each tile processed is classified.

Figure 17B:
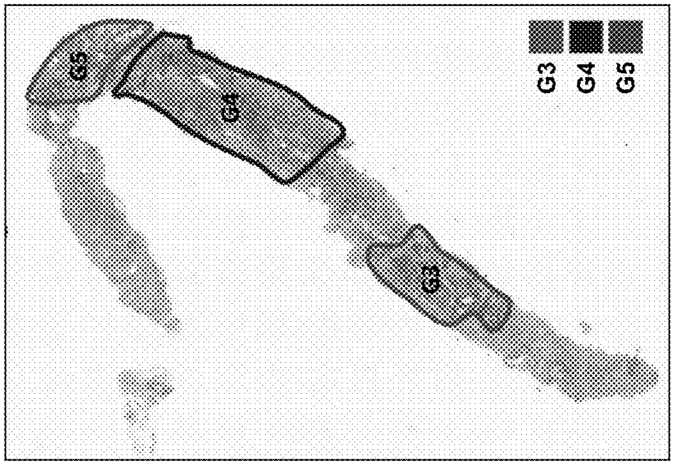
FIG. 17B illustrates an exemplary Gleason mask provided in accordance with an embodiment of the present disclosure.
Figure 17A:
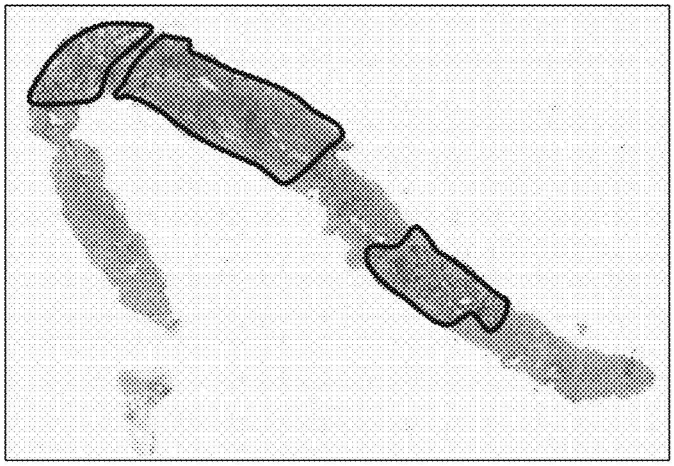
FIG. 17A illustrates an exemplary cancer mask provided in accordance with an embodiment of the present disclosure.

The machine learning element 114 also provides a WSI classification associated with the whole slide. As noted above, this classification is either benign or cancer. As noted above, the WSI classification may be based on clustering of the tile level information, that is the first image information, second image information, etc. As is noted above, the clustered information is used to generate a histogram associated with the whole slide image such that a determination of the classification of the whole slide. In particular, the histogram may be provided as in input to a second machine learning algorithm trained using the whole slide training information of the first training step to classify the whole slide as either benign or cancerous. In embodiments, the machine learning element 114 further provides the mask information discussed above with reference to step S404 based on additional processing of the classified image information. In embodiments, the mask information may provide a cancer mask contrasting benign tissue from cancerous tissue as generally illustrated in FIG. 17A. In embodiments, the mask information may provide a Gleason mask that contrasts benign tissue, Gleason 3 tissue, Gleason 4 tissue and Gleason 5 tissue as illustrated in FIG. 17B. In embodiments, the mask information is generated by stitching together the tile-by-tile image information and classifications to provide a mask overlay for the whole slide to highlight high cancer risk areas and specific Gleason scores. In embodiments, the mask information is provided to a user interface that may be presented on a display element 118 operably connected to the machine learning element 114. In embodiments, the display element 118 may be wirelessly connected to the machine learning element 114. In embodiments, the mask information may be generated by a processor separate from the machine learning element 114. In embodiments, the mask information may be provided to the display 118 via the separate processor or may be provided via the machine learning element 114. In embodiments, the mask information may be stored in memory before, after or instead of displaying it. In embodiments, FIG. 18 illustrates an exemplary user interface that may be provided on the display 118. In addition to showing the WSI along with the mask information, the user interface may present additional information including the WSI classification as well as certain morphological features. In embodiments, display 118 may be a touch-screen or may be operably connected to one or more input devices to allow a user to interact with the image information and mask information. As noted above, a user may modify mask information. In embodiments, the user may measure or otherwise highlight particular structures or morphological features and may provide notes or observations that are stored with the image information and mask information. As illustrated in FIG. 18, the display may be used to enhance portions of the WSI and/or the mask for further study.

In embodiments, the mask information and image data may be stored in memory 122, which may allow for storage of objects and text. In embodiments, the memory 122 may be a database, a cloud storage system, such as Amazon's MongoDB. In embodiments, providing for cloud storage of the mask information and image information simplifies remote access to this information and allows remote viewing and diagnosis. In embodiments, the display 118 may be positioned remotely to allow a user to view the WSI and mask information in virtually any location.

In embodiments, the first training set may be provided via a laboratory information system LIS 120. In embodiments, the first training set may be provided in any suitable manner, for example, via transmission over a network or the internet. In embodiments, patient information may be proved via the LIS 120 as well, however, patient information may be provided in any suitable manner. In embodiments, the pathologist may tag slides associated with prostate tissue including indications of Gleason Scores using the LIS 20. In embodiments, the slide may be broken up into training crops and tagged training crops as well as whole slide training information may be stored as the training set as noted above with respect to FIG. 6. In embodiments, the training set may be stored in the memory 122 which includes both object information and text. In embodiments, the image information and classification information may be stored in the memory 122 as noted above. In embodiments, the LIS 120 may also be used to provide patient information which may be stored in the memory 122 and associated with the image information and the mask information associated with the tissue sample of the patient. In embodiments, the memory 110 may be separate from the memory 122, for example, the memory 110 may be S3 while the memory 122 may be the MongoDB. In embodiments, memory 110 may be the same as memory 122. In embodiments, additional memory may be provided.

In embodiments, the machine learning element 114 may be a server connected to a communication network, for example, the Internet, a local area network, a secure network, to name a few. In embodiments, the machine learning element 114 may be a computer system including a processor and memory operably connected thereto and configure to implement the first machine learning algorithm and the second machine learning algorithm. In embodiments, the use of AWS resources allows the system 100 to be implemented as a web application. In embodiments, the system 100 need not be implemented on the web but may be implemented on a local network or on an internal computer system.

In embodiments, the method and system of the present disclosure provides a high level of precision and detects even small areas of cancerous tissue that may be undetected by a pathologist. As noted above the method and system of the present disclosure achieve an AUC of 0.98 in detecting tumor regions.

The method and system identify areas that are linked to distinct Gleason scores enabling the platform to deliver a more objective evaluation of the prostate core needle biopsy.

The method and system allow for computation of the area corresponding to each Gleason score on every prostate slide allowing for a conclusive Gleason Score since the Gleason mask provides for a clear indication of the amount of each Gleason score present. The method and system also allows for identification of morphological features such as tumor area, tumor length and tumor percentage.

The method and system substantially reduce the time needed to analyze a slide, typically providing comprehensive analysis in just 8 minutes.

In regions with limited access to experienced pathologists, the method and system provide a valuable tool to provide guidance and assistance to less-experienced pathologists, thus expanding access to expertise and addressing the problem of limited availability of specialized pathologists.

It is understood that the examples and embodiments described herein are for illustrative purposes only and that various modifications or changes in light thereof will be suggested to persons skilled in the art and are to be included within the spirit and purview of this application and scope of the appended claims. Further, it is understood that examples and embodiments described herein with reference to diagnosis do not limit the scope of the appended claims and instead are illustrative of examples and embodiments.

Now that embodiments of the present invention have been shown and described in detail, various modifications and improvements thereon can become readily apparent to those skilled in the art. Accordingly, the exemplary embodiments of the present invention, as set forth above, are intended to be illustrative, not limiting. The spirit and scope of the present invention is to be construed broadly.

What is claimed is:

1. A method for classifying morphology based on pathological slides comprising:

a. obtaining first image information associated with a first pathological slide of tissue, wherein the pathological slide is divided into a plurality of tiles and the first image information is associated with a first tile of the plurality of tiles and second image information is associated with a second tile of the plurality of tiles;

b. classifying the first image information using a first machine learning algorithm trained using a first training set, where the first image information is an input, and the machine learning algorithm provides first classification information indicating morphology of the tissue associated with the first image information;

c. generating mask information indicating morphology patterns of the tissue based on the first classification information provided in the classifying step;

d. providing the mask information to a user interface, wherein the user interface is configured to display the first image information and the mask information to highlight portions of the first image information associated with morphology of the tissue;

e. repeating steps (a) to (d) for the second image information and respective image information associated with each tile of the plurality of tiles; and f. classifying a whole slide image of the pathological slide associated with the first image information, second image information and respective image information based on the first image information, the second image information and the respective image information associated with each tile of the plurality of tiles wherein a single classification is provided for the whole slide.

2. The method of claim 1, wherein the first image information is obtained from a database.

3. The method of claim 1, wherein the first image information is obtained from a cloud storage system.

4. The method of claim 1, wherein the first image information is provided in a format compatible with the machine learning algorithm.

5. The method of claim 1, wherein the first image information includes slide ID information associated with a respective slide associated with the first image information and tile location information associated with a position of the tile in the respective slide.

6. The method of claim 1, wherein the mask information includes mask information highlighting at least one of cellular patterns and histology patterns.

7. The method of claim 1, wherein the whole slide image classification is based on a whole slide image histogram that provides a vector associated with the whole slide image and is provided as an input to a second machine learning algorithm trained by prior whole slide image histograms to provide a whole slide image classification.

8. The method of claim 7, further comprising storing the first image information, the second image information, the respective image information, the mask information and the whole slide image classification in memory configured to store objects and text.

9. The method of claim 1, wherein the first training set is stored in memory configured to store objects and text.

10. A system for classifying morphology of tissue based on pathologic slides of the tissue comprises:

a. first memory configured to store image information associated with a histopathologic slide;

b. a formatter dividing the image information associated with the histopathological slide into a plurality of tiles and storing respective image information associated with each tile in the first memory, wherein first image information is associated with a first tile and second image information is associated with a second tile;

c. a machine learning element configured to classify the image information based on morphology and operably connected to the first memory, the machine learning element including:

one or more processors; and second memory operably connected to the one or more processors and including processor executable code that when executed by the one or more processors, causes the one or more processors to perform steps of:

i. obtaining the first image information from the first memory;

ii. classifying the first image information using a first machine learning algorithm trained using a first training set, where the first image information is an input, and the machine learning algorithm provides first classification information indicating morphology of tissue associated with the first image information;

iii. generating mask information indicating morphology patterns of the tissue based on the first classification information provided in the classifying step; and iv. providing the mask information to a user interface, wherein the user interface is configured to display the first image information and the mask information to highlight portions of the first image information associated with morphology of tissue on an electronic display operably connected to the machine learning element;

V. repeating steps (i) to (iv) for the second image information and the respective image information associated with each tile of the plurality of tiles; and vi. classifying a whole slide image of the histopathological slide associated with the first image information, second image information and the respective image information based on the first image information, the second image information and the respective image information wherein a single classification is provided for the whole slide.

11. The system of claim 10, wherein the first memory is one of a database and a cloud storage system.

12. The system of claim 10, wherein the first image information includes slide ID information associated with a respective slide associated with the first image information and tile location information associated with a position of the first tile in the respective slide.

13. The system of claim 10, wherein the mask information includes mask information highlighting at least one of cellular patterns and histology patterns.

14. The system of claim 10, further comprising a second memory configured to store objects and text, wherein the first image information, the second image information, the respective image information, mask information and whole slide image classification are stored in the second memory configured to store objects and text.

15. The system of claim 10, further comprising a second memory configured to store objects and text, wherein the first training set is stored in the second memory configured to store objects and text.

* * * * *